United States Patent [19]

Milosevic et al.

[11] Patent Number: 5,035,504
[45] Date of Patent: Jul. 30, 1991

[54] LIQUID ANALYSIS WITH INTERNAL REFLECTION SPECTROSCOPY

[75] Inventors: Milan Milosevic, Fishkill, N.Y.; Nicolas J. Harrick, Croton Dam Rd., Ossining, N.Y. 10562

[73] Assignee: Nicolas J. Harrick, Ossining, N.Y.

[21] Appl. No.: 512,451

[22] Filed: Apr. 23, 1990

[51] Int. Cl.⁵ .............................................. G01J 3/42
[52] U.S. Cl. ..................................... 356/300; 356/244
[58] Field of Search ................ 356/300, 244, 246, 440

[56] References Cited

U.S. PATENT DOCUMENTS 3,393,603  7/1968  Harrick ............................... 356/246
3,669,545  6/1972  Gilby .................................. 356/300
4,602,869  7/1986  Harrick ............................... 356/246
4,730,882  3/1988  Messerschmidt ..................... 356/300

OTHER PUBLICATIONS

Korolev et al., Instruments and Experimental Techniques (Trans. of: Prib. and Tekh. Eksp. (USSR)) vol. 17, No. 4, pt 2, pp. 1232-1234, Jul.-Aug. 1974 (publ. Jan. 1975).

*Primary Examiner*—F. L. Evans

[57] ABSTRACT

Novel internal reflection plates and spectroscopy systems using such plates especially for analyzing liquids. The plates have a generally trapezoidal shape with beveled ends, and are oriented relative to an incident radiation beam such that the beam reflects from the bevel and propagates down the plate by multiple internal reflections form its major surfaces.

20 Claims, 2 Drawing Sheets

LIQUID ANALYSIS WITH INTERNAL REFLECTION SPECTROSCOPY

This invention relates to internal reflection spectroscopy (IRS), and in particular to the application of this analysis technique to the analysis of liquids.

BACKGROUND OF THIS INVENTION

Reference is made to a book authored by N. J. Harrick entitled "Internal Reflection Spectroscopy", published by Interscience Publishers in 1967. This book provides a complete description of the principles underlying this technology, and also describes the construction and configuration of so-called internal reflection elements (IREs) used in such analysis equipment. Attention is especially drawn to pages 223-227 which describes the application of IREs for use in liquid cells. Reference is further made to U.S. Pat. Nos. 3,393,603; 4,602,869; and 4,730,882, which are also directed to different IRE and liquid cell geometries.

In general, it is important to many companies that process liquids to be able to conduct in-line analysis or analysis of samples in the simplest and most economic manner. As is known, many conventional spectrometers generate a radiation beam which upon emerging from the instrument converges to a region in the so-called sampling space or compartment of the instrument, and if not intercepted or used will continue back into the instrument for spectral analysis. It is common to locate the IRE element or transfer optics for the IRE element in the sampling space so as to maintain the original focussing conditions. At the same time, it is desirable that the IRE element, which must physically contact the liquid, be suitably positioned for effective and efficient use.

SUMMARY OF INVENTION

One object of the invention is an IRE construction that is suitable for in-line analysis of materials.

Another object of the invention is a spectroscopic system especially suited for in-line analysis of flowing liquids.

Still another object of the invention is an IRE and liquid sampling attachment for IRS using the IRE which is simple to use while maintaining the original focussing conditions of the spectrometer.

There and other objects and advantages of the invention are achieved in accordance with one feature of the invention with a novel plate-like IRE that is configured to be placed inside a space containing a liquid to be analyzed. The novel IRE allows entrance of the analyzing radiation via a side edge and employs a compound beveled surface to redirect the beam to propagate down the plate via multiple internal reflections from its front and back major surfaces until it again encounters a compound bevel and exits via the same side edge.

In accordance with another feature of the invention, a novel plate-like IRE is configured to mount on an apertured member such that a major surface of the IRE is oriented horizontally and accesible for receiving a sample of a liquid or other material to be analyzed. In this case, the radiation beam enters via a beveled surface and after undergoing several preliminary reflections propagates down the plate via multiple reflections from its major surfaces, before exiting via a beveled surface at the opposite end.

With both embodiments, the advantages is obtained that only a single flat reflector is necessary to direct the IRS beam into the IRE, and only a single flat reflector is necessary to redirect the exiting beam back into the instrument. Moreover, both embodiments are very easy to use and align, and give excellent spectra of any contacting liquid due to the multiple interactions of the beam with the liquid or other material or a sample thereof.

SUMMARY OF DRAWINGS

The invention will now be described in further detail with respect to several preferred embodiments, taken in conjunction with the accompanying drawings, wherein.

DETAILED DESCRIPTION OF PREFERRED EMBODIMENTS

Figure 1:
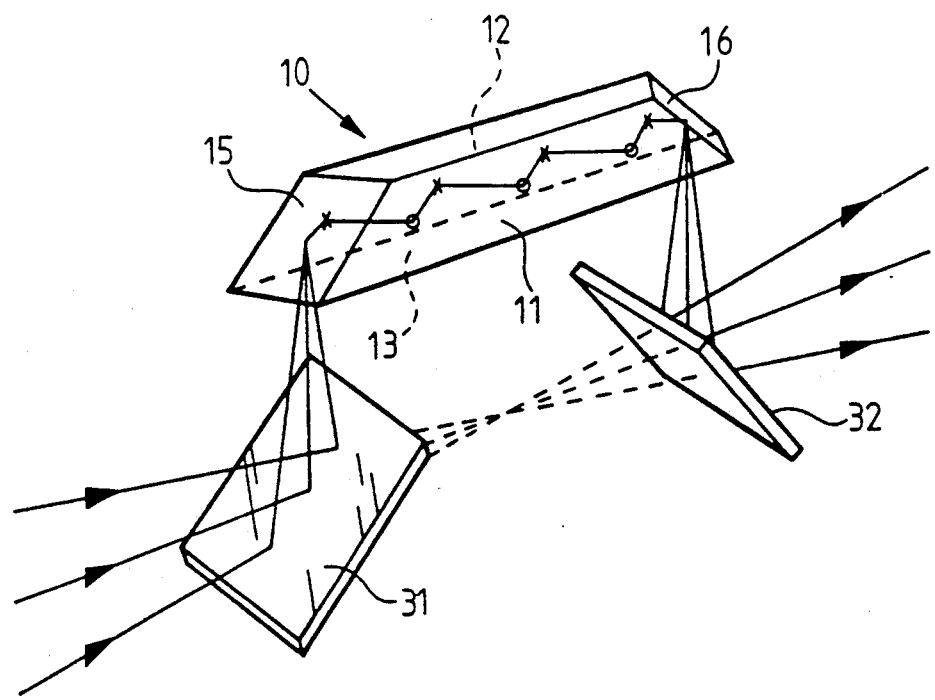
FIG. 1 is a perspective view of one form of IRE with beam directing means for direct immersion in a liquid to be analyzed.

FIG. 1 illustrates an IRE in accordance with the invention for direct immersion into a liquid to be analyzed. The IRE 10 is a thin plate-like member having flat major surfaces 11 and 12, herein also referred to as front and back surfaces as will be clear from FIG. 2, flat edge surfaces 13 and 14, herein also referred to as bottom and top surfaces, and beveled end surfaces 15 and 16. The plate 10 has a generally trapezoidal shape. All the surfaces shown are polished flat. The front and back surfaces 11, 12 are parallel, as are the top and bottom edge surfaces 13, 14, and the latter are also at right angles to the former. The ends 15, 16 have a compound bevel, meaning that the surfaces 15, 16 are flat and are ground to be inclined at an angle of 45° to both the bottom edge surface 13 and the front surface 11.

Figure 2:
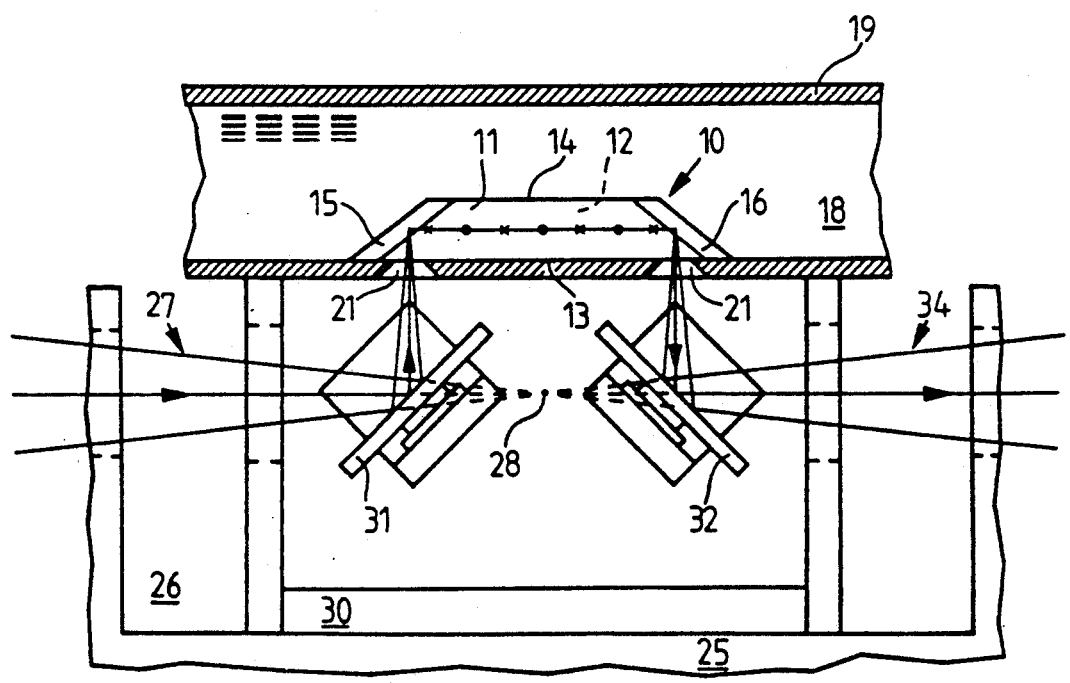
FIG. 2 is schematic side view showing how the IRE of FIG. 1 would be used in IRS.

FIG. 2 shows how the IRE 10 is used as a single pass, multiple reflecting plate. As one example, a liquid 18, say, is flowing along a pipe or conduit 19. Two openings 21 are formed at the bottom wall of the pipe 19. The IRE crystal 10 is sealed to the wall of the conduit 19 either via suitable gaskets or is cemented to the wall by an epoxy or other adhesive, in a vertical position with its bottom edge 13 overlying the conduit openings 21. The conduit openings 21 expose the bottom edge 13 through the openings. If not cemented, the IRE 10 can be held down in the position shown by any suitable means.

A suitable spectrometer 25 is shown schematically, positioned such that its sampling compartment 26 is located below the IRE 10. Many spectrometers of the dispersion type or Fourier type are suitable. It is assumed, as is common, that a generally converging radiation beam 27 enters the sampling compartment 26. If untouched, as shown by the dashed lines, it would focus to a point 28 and then diverge and continue on its path back into the spectrometer for detection and processing. An IRS attachment 30 is provided in the sampling compartment 26, and supports at a 45° angle two plane mirrors 31, 32. The geometry is chosen such that the horizontal optical path between the mirrors is just equal to the sum of the two optical paths from each mirror to the bottom edge 13 of the IRE 10. This will maintain the original focussing conditions within the sampling compartment of the spectrometer. The first plane mirror 31 redirects the beam 27 upward so that it passes through the left opening 21 to impinge generally orthogonally with few losses on the bottom edge surface 13. Although generally orthogonal impingement of the light is preferred, other angles can be used when there is a need to do so. The beam then enters the IRE and internally reflects off of the compound beveled surface 15, which directs it into a horizontal plane at an angle of 45° to the front and back surfaces 11, 12. Since for most IRE materials, a 45° angle exceeds the critical angle, the beam zig-zags in a horizontal plane by multiple internal reflections off of the front and back surfaces 11, 12—indicated by the row of circles and Xs—and thus propagates down the plate 10 until it arrives at the right beveled surface 16, from which it internally reflects again in two direction and is thus directed downwardly, exits from the bottom edge 13 with few losses and passes through the right opening 21 toward the second mirror 32. After reflection from the second mirror, the beam 34 is redirected back into the spectrometer along the same path that would have been followed had the attachment 30 not been present. In this instance, the IRE plate acts as a light pipe, so that its length need not be taken into account in determining the necessary optical path lengths to maintain the focussing conditions as shown.

Since the liquid 18, which may be still or flowing, is present on both sides of the plate 10 and contacts both the front and back surfaces 11, 12, the usual frustrated total reflection interaction will occur at the front and back surfaces with selected beam wavelengths thereby modulating the beam, so that the exiting beam 34 will contain analysis information about the liquid. The result is that, if the pipe 19 is carrying a liquid undergoing processing, the system illustrated provides in-line, real-time analysis of properties of the liquid 18, which can be directly used to vary operating parameters of the liquid processing.

There are also other advantages of the system described. Since the beam will interact with any material in contact with a surface region from which the beam internally reflects, if it is not the material being analyzed, undesirable spurious spectra will result. In the system illustrated in FIG. 2, it will be noted that the only non-sample contact with the IRE is made by any seals or adhesives at the bottom edge 13. But, the internal reflections are from the beveled ends 15, 16 and from the front and back surfaces 11, 12 and do not reflect from the surface regions on the bottom edge that may be contacted. Hence, no spurious spectra are produced.

Another advantage of the IRE of FIG. 1 is its streamlined shape, which presents virtually no resistance to liquid flow. When mounted vertically as shown, the lead bevel edge allows free flow of liquid past it. Moreover, the thickness between the front and back surfaces can be maintained small, for example, about 6 mm. A typical IRE plate would have a height dimension of about 10 mm, and a length of about 60 mm, allowing a total of 10 internal reflections from the front and back surfaces. Thus, high sensitivity is obtained producing excellent spectra, even with liquids of low absorption, while allowing full flow of the liquid past the IRE. It thus lends itself well to in-flow studies of liquids, and operation in high pressure vessels or pipes. With the transfer optics illustrated in FIG. 2—other optical geometries are also possible—the IRE therefore is positioned outside the sampling compartment, which also makes for easier operation of the spectrometer. While the compound bevel ends are preferably selected to reflect the incoming light to produce an angle of incidence on the sampling surfaces 11 and 12 to be 45° as described, other compound bevels that will produce angles of incidence on the said surfaces 11 and 12 in the range of 20°-70° can also be used, provided that the critical angle is exceeded. The angle formed by the end beveled surfaces is difficult to specify, because of its compound nature, but it will generally correspond to the chosen angle of incidence for the beam on the sampling surfaces. Thus, if the angle of incidence is chosen as 45°, the entrance edge 15 will be cut so that the incoming beam will reflect from it at a 45° angle, and the exit edge 16 will be correspondingly cut so that the propagating beam reflects from it also at an angle of 45°. The dimensions given are just exemplary, and other proportions of the IRE will obviously also be suitable.

Figure 3:
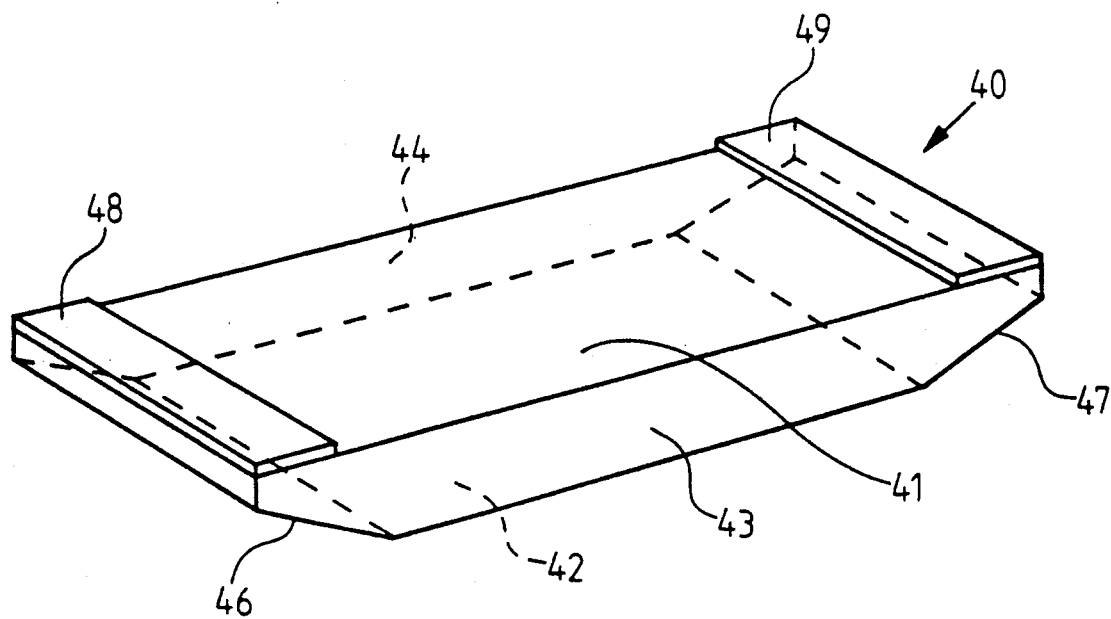
FIG. 3 is a perspective view of one form of IRE for IRS analysis of a sample of a liquid.
Figure 4:
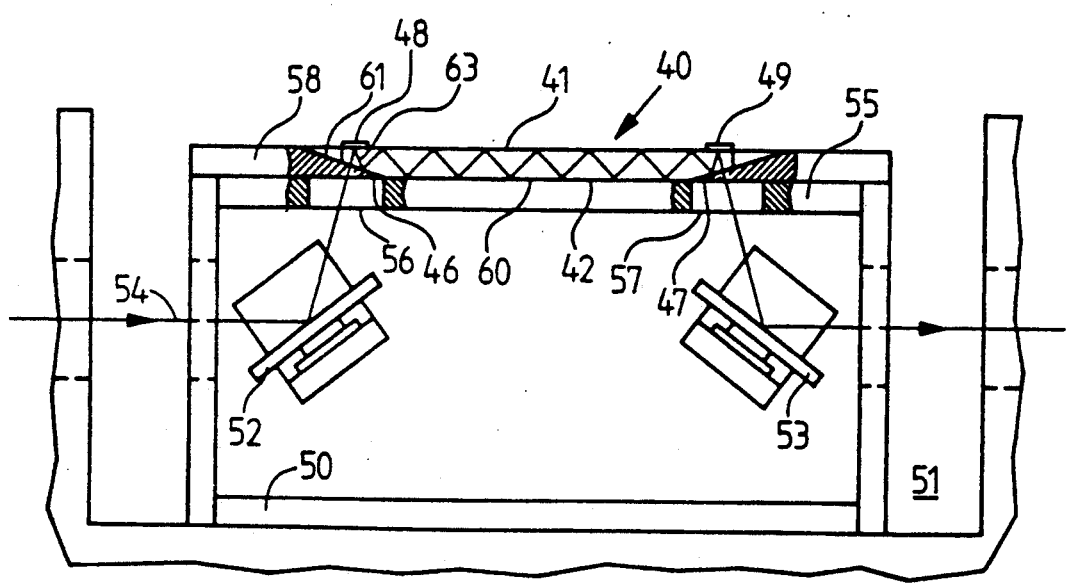
FIG. 4 is a view similar to FIG. 2 showing how the IRE of FIG. 3 is used.

While the embodiment of FIGS. 1 and 2 is well-suited for in-line liquid analysis, the embodiment of FIGS. 3 and 4 is for use with a sample of the liquid or a solid to be analyzed. The IRE 40 has a generally trapezoidal shape comprising major top 41 and bottom 42 planar surfaces, and side edges 43, 44. The top and bottom surfaces 41, 42 are parallel, as are the side edges 43, 44, which are oriented at right angles to the former. Simple beveled surfaces 46, 47 are provided at opposite ends. The bevels 46, 47 can form angles with the top major surface 41 of between about 10° and 20°, with 15° being preferred. Two thin narrow metallization strips 48, 49 are deposited on the top surface 41 so as to overlie, respectively, the left 46, and right 47 bevels. All surfaces are polished flat and the metallized strips form good mirrors.

FIG. 4 shows the operation. In this case, the IRE 40 is part of an attachment 50 which is mounted in the sampling compartment 51 of the spectrometer. As before, transfer optics comprising two plane mirrors 52, 53 are supported by the attachment so as to redirect the spectrometer beam 54 upward. The upper part of the attachment comprises a horizontal support plate 55 with openings 56, 57 for passage of the radiation beam, and an upper horizontal member 58 for supporting the IRE 40. The upper member 58 comprises a plate with a center rectangular opening 60 having a beveled shoulder 61 for supporting the IRE 40 in the horizontal position shown.

The radiation beam reflected from the mirror 52 enters the left beveled end 46 substantially orthogonally and reflects from the metallized layer 48 such that the reflected beam 63 is incident on the bevel surface 46 at an angle exceeding the critical angle, internally reflects from the bevel 46 and is incident on the top surface 41 at an angle exceeding the critical angle, and as shown then internally reflects from the bottom 42 and top 41 surfaces and thus propagates to the right down the IRE 40. The beam then undergoes a similar reflection pattern at the right end internally reflecting from the right bevel 47, then from the metallization 49, and exits substantially orthogonally from the bevel 47. The beam then reflects from the right mirror 53 and is back in line with the entering beam 54 and reenters the spectrometer for detection and processing. A sample placed upon the top surface 41 of the IRE will thus interact with the multiply-reflecting radiation beam thereby modulating it with information about the sample properties.

The bevel angles with the top surface 41 can vary over a range of about 10°–20°. The angle of 15° is preferred, because this value together with the first reflection from the metallization 48 and the successive second reflection from the bevel 46 are additive and as a result the beam internally reflects from the top 41 and bottom 42 surfaces at 3 times 15°=45°. The metallization is required because, for most IRE materials, the 15° angle of incidence does not exceed the critical angle, whereas the angle of incidence at the bevel 46 on the second reflection is 30°, which does exceed the critical angle. The same angular relationships also exist at the right end of the IRE 40. As with the FIG. 2 embodiment, the focussing conditions of the spectrometer are maintained.

While the FIGS. 3 and 4 embodiment are well suited for liquid samples, it is also usable with any sample material including solids and powders that can be placed on the IRE's top surface 41 and form a sufficiently intimate contact with the surface that the sample material will interact with the evanescent wave emanating from the internally reflecting radiation beam.

Typical dimension for the plate 40 would be a length of about 57 mm, a width, the other dimension of the major surfaces, of about 10 mm, and a thickness of about 3 mm. Other proportions will also be suitable.

The IREs of the invention can be constituted of any of the materials described in the Harrick book, and are useful with any of the radiations conventionally used in this field, including IR, UV and visible.

While the invention has been described in connection with preferred embodiments, it will be understood that modifications thereof within the principles outlined above will be evident to those skilled in the art and thus the invention is not limited to the preferred embodiments but is intended to encompass such modifications.

What is claimed is:

1. An internal reflection spectroscopy system comprising:
   an internal reflection plate generally of the trapezoidal type having a length dimension, a height dimension, and a thickness dimension and having substantially parallel, major front and back surfaces generally defined by the plate's length and height dimensions, substantially parallel, bottom and top edge surfaces generally defined by the plate's length and thickness dimensions, and left and right side edge surfaces generally defined by the plate's height and thickness dimensions, said side edge surfaces being compound beveled and each forming with the front surface an angle in the range of about 20°–70°,
   means for supporting the internal reflection plate in such manner that at least one major surface is substantially exposed to receive a sample to be analyzed,
   first means for directing an incident radiation beam to one of the top and bottom edge surfaces such that the beam enters the plate and directly impinges on one of the beveled surfaces at one end and is reflected from that beveled surface and propagates down the plate by multiple internal reflections from the plate's front and back major surfaces until the beam reflects from the beveled surface at the opposite end and exits the plate via one of its top and bottom edges,
   second means for receiving the beam exiting from the plate and re-directing it.

2. An internal reflection spectroscopy system as claimed in claim 1, wherein the first and second means are plane mirrors.

3. An internal reflection spectroscopy system as claimed in claim 1, wherein the first means are positioned to direct the incident beam substantially orthogonally to the bottom edge surface.

4. An internal reflection spectroscopy system as claimed in claim 1, wherein the compound beveled surfaces are cut so as to cause an incident beam reflected therefrom to impinge on the front and back surfaces at an angle of incidence of about 20°–70°.

5. The system of claim 1, wherein the support means comprise means for supporting the plate in a vertically-oriented position with said bottom edge surface being down and receiving the incident radiation beam, and with the radiation beam exiting from the said bottom edge.

6. The system of claim 1, wherein the beveled surfaces are oriented at about 45° with respect to both a major surface and an edge surface of the plate.

7. The system of claim 1 in combination with a container for a liquid to be analyzed, said container having openings for allowing a radiation beam to enter and exit from the container, said plate being mounted within the container over the container's openings, and means for sealing the plate to the container at the openings such that the plate's bottom edge surface portions opposite their respective beveled ends are exposed for respectively receiving and transmitting the radiation beam via a respective container opening.

8. The system of claim 1, wherein the plate is oriented vertically with its front and back surfaces exposed.

9. An internal reflection element for use in internal reflection spectroscopy, said internal reflection element being generally of the trapezoidal type having a length dimension, a height dimension, and a thickness dimension and having substantially parallel, major front and back surfaces generally defined by the plate's length and height dimensions, substantially parallel, bottom and top edge surfaces generally defined by the plate's length and thickness dimensions, and left and right side surfaces edge generally defined by the plate's height and thickness dimensions, said side edge surfaces being compound beveled and each forming with the front surface an angle in the range of about 20°–70°.

10. The element of claim 9, wherein the side edge surfaces form with the front surface and bottom edge an angle of about 45°.

11. An internal reflection element as claimed in claim 9, wherein the compound beveled surfaces are cut so as to cause an incident beam reflected therefrom to impinge on the front and back surfaces at an angle of incidence of about 20°–70°.

12. A element as claimed in claim 11, wherein the front and back surfaces are parallel.

13. An internal reflection spectroscopy system comprising:
   an internal reflection plate generally of the trapezoidal type having a length dimension, a width dimension, and a thickness dimension and having substantially parallel, major top and bottom surfaces generally defined by the plate's length and width dimensions, substantially parallel, front and back edge surfaces generally defined by the plate's length and thickness dimensions, and left and right side edge surfaces generally defined by the plate's width and thickness dimensions, said side edge surfaces being simple beveled and each forming with the top surface an angle in the range of about 10°-20°, means for supporting the internal reflection plate in such manner that at least one major surface is substantially exposed to receive a sample to be analyzed, reflecting strips on a major surface overlying the side edge surfaces, first means for directing an incident radiation to one of the side edge surfaces such that the beam enters the plate and directly impinges on one of the reflecting strips, reflects from the said reflecting strip to directly impinge on said one beveled surface and is reflected from that beveled surface and propagates down the plate by multiple internal reflections from the plate's top and bottom major surfaces until the beam reflects from the beveled surface and the reflecting strip at the opposite end and exits the plate via one of its side edges, second means for receiving the beam exiting from the plate and redirecting it.

14. An internal reflectance spectroscopy system as claimed in claim 13, wherein said first and second means comprise plane mirrors.

15. The system as claimed in claim 13, further comprising means for supporting the plate in a horizontal position with its top surface exposed to receive a sample to be analyzed.

16. The system of claim 13, wherein said beveled surfaces each form an angle of about 15° with the top surface.

17. An internal reflectance spectroscopy system as claimed in claim 13, wherein said reflecting strips comprise metallizations.

18. An internal reflection element for use in internal reflection spectroscopy, said internal reflection element being generally of the trapezoidal type having a length dimension, a width dimension, and a thickness dimension and having substantially parallel, major top and bottom surfaces generally defined by the plate's length and width dimensions, substantially parallel, front and back edge surfaces generally defined by the plate's length and thickness dimensions, and left and right side edge surfaces generally defined by the plate's width and thickness dimensions, said side edge surfaces being simple beveled and each forming with the top surface an angle in the range of about 10°-20°.

19. An internal reflection element as claimed in claim 18, wherein the beveled surfaces form a 15° angle with the top surface.

20. An internal reflection element as claimed in claim 18, further comprising two narrow spaced metallization strips on the top surface each in a position overlying only one of the beveled edges.

* * * * *